US00PP16124P3

(12) United States Plant Patent
Hunter et al.

(10) Patent No.: US PP16,124 P3
(45) Date of Patent: Nov. 22, 2005

(54) 'HW616' PEAR

(50) Latin Name: *Pyrus communis*
Varietal Denomination: HW616 Pear

(75) Inventors: David Michael Hunter, St. Catharines (CA); Frank Kappel, Summerland (CA); Harvey Allen Quamme, Penticton (CA); William Gordon Bonn, Windsor (CA)

(73) Assignee: Agriculture and Agri-Food Canada, Ontario (CA)

( * ) Notice: Subject to any disclaimer, the term of this patent is extended or adjusted under 35 U.S.C. 154(b) by 530 days.

(21) Appl. No.: 10/190,392

(22) Filed: Jul. 3, 2002

(65) Prior Publication Data

US 2004/0006799 P1 Jan. 8, 2004

(51) Int. Cl.[7] ..... A01H 5/00
(52) U.S. Cl. ..... Plt./176
(58) Field of Search ..... Plt./176

*Primary Examiner*—Bruce R. Campell
*Assistant Examiner*—Michelle Kizilkaya
(74) *Attorney, Agent, or Firm*—Flynn, Thiel, Boutell & Tanis, P.C.

(57) ABSTRACT

'HW616' is an early season high quality pear primarily for the fresh market that has an attractive golden yellow fruit with no blush, smooth skin, very good balance between sweetness and acidity, that is exceptionally juicy and has excellent resistance to natural fire blight.

1 Drawing Sheet

Genus and species: *Pyrus communis* L.

FIELD OF THE INVENTION

The present invention relates to a variety of a pear tree and more specifically to a pear tree variety that yields a high-quality, early season pear for the fresh market.

BACKGROUND OF THE INVENTION

The variety 'HW616' was developed by Agriculture and Agri-Food Canada at Harrow, Ontario. The variety has been described by Hunter et al, HortScience, Vol. 37 (1):224–226, February 2002. To applicants' knowledge, the variety has not been made publicly available. It will be marketed under the brand name AC HARROW GOLD.

SUMMARY OF THE INVENTION

The new and distinct pear variety, which has been given the designation of 'HW616', produces a high quality early season pear primarily for the fresh market. 'HW616' is picked about ten days before 'Bartlett' (unpatented), the reference cultivar it most closely resembles. 'HW616' has an attractive golden yellow (RHS color designations fruit with no blush, smooth skin, very good flavor with a good balance between sweetness and acidity, and exceptionally juicy. Fruit size of 'HW616' is equivalent to that of 'Bartlett'. The tree of 'HW616' is medium in size, upright to spreading. 'HW616' has excellent resistance to natural fire blight (*Erwina amylovora*) infections (9.6 rating), whereas 'Bartlett' is susceptible to natural infections (4.2 rating). The response to infection following inoculation with the causative organism is more severe in 'Bartlett' (mean lesion length 63% of shoot length, with some lesions extending into subtending woody tissues) than in 'HW616' (mean lesion length 25% of shoot length, maximum lesion length of 52% of shoot length).

DETAILED DESCRIPTION OF THE VARIETY

Figure 1:
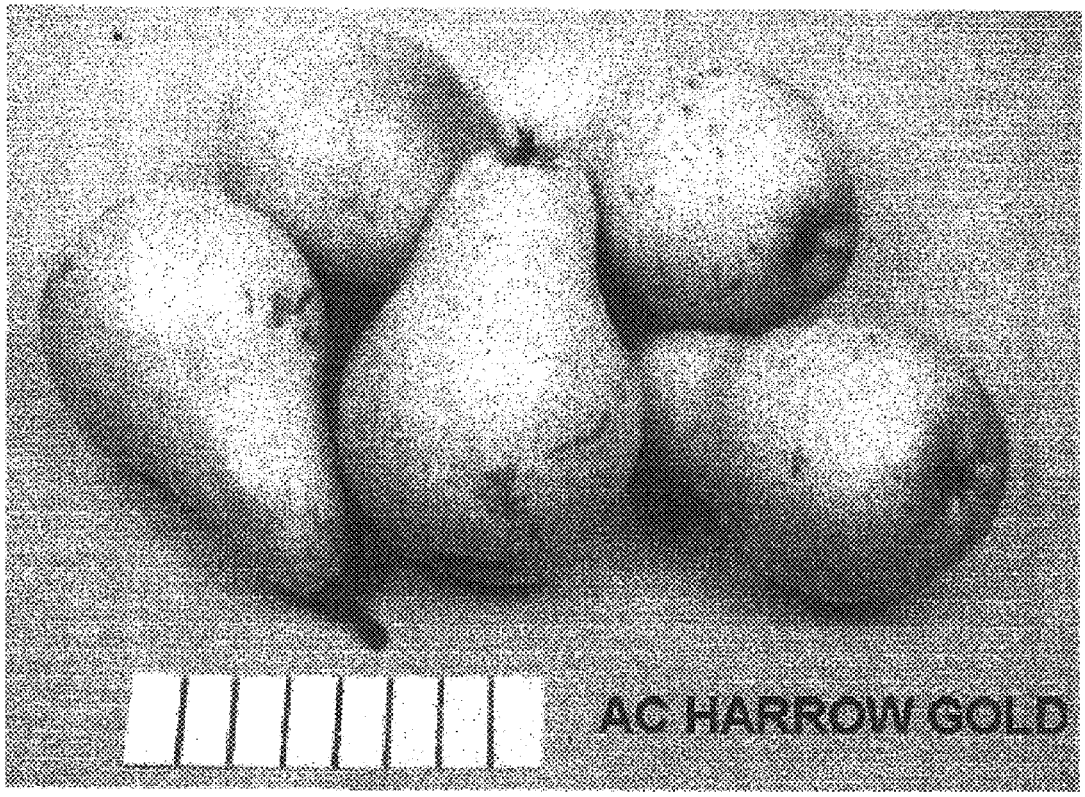
FIG. 1 is a photographic illustration of the whole fruit of 'HW616' pear. The fruits depicted in FIG. 1 were obtained from mature (~10 years old) trees of the variety grown on 'Bartlett' seedling rootstock at the AAFC Research Centre, Harrow, Ontario, Canada. These are the same trees used to obtain the botanical description data herein.

'HW616' resulted from a controlled cross between 'Harvest Queen' (unpatented) and 'Harrow Delight' (unpatented) made in 1975 by Dr. H. A. Quamme at the Agriculture and Agri-Food Canada Research Centre at Harrow, Ontario. It was selected as a hybrid seedling (H7535-100) in 1983 by F. Kappel, and propagated by budding onto pear seedling rootstocks. In 1985, it was advanced and testing began in 1987 at the Harrow Research Centre. Propagation for regional trials in cooperation with the Western Ontario Fruit Testing Association began in 1985, and test trees were placed in regional trials beginning in 1987. Evaluations of second test orchards have been conducted by F. Kappel and D. M. Hunter, and W. G. Bonn has evaluated disease resistance.

Asexual propagation maintains uniformity and stability of 'HW616'. No variants, off-types or mutants have been observed. The variety will be maintained at the Agriculture and Agri-Food Canada Harrow Research Centre in a virus tested budwood orchard, and in the holdings of the Canadian Clonal Gene bank.

The color terminology is in accordance with The Royal Horticultural Society (R.H.S.) Colour Chart.

Description and performance: Tree characteristics:

*Tree habit and productivity.*—The tree of 'HW616' is medium in size, upright to spreading, annually productive and winter hardy. In 1994 at Harrow, following winter minimum temperatures as low as −29°

C., a full crop was produced by the original seedling tree, as well as by trees grown on 'Bartlett' seedling rootstock. The original seedling tree has consistently produced good crops with no evidence of biennial bearing. Precocity of 'HW616' trees propagated on 'Bartlett' seedling rootstock appears to be similar to that of 'Bartlett', with bearing initiated ≈4 years after planting. Annual yields in the early year of production have been slightly lower than those of 'Bartlett', except when fire blight infections have reduced 'Bartlett' performance.

*Shoot habit.*—The bark on the sun-exposed side of dormant shoots is light brown with olive (RHS 199A, Royal Horticultural Society, 1966). The diameter of dormant shoots of 'HW616' is similar to that of 'Bartlett'. Mean internode length of 'HW616' was similar to 'Bartlett', 'Harrow Delight', and 'Harrow Sweet' (patented), but shorter than 'Harvest Queen' and 'Bosc' (patented) (Table 1).

TABLE 1

Mean internode length (cm ± SE) as determined on five successive internodes from the midportion of 1-year-old shoots.

| Cultivar | Internode length | No. of Shoots |
|---|---|---|
| 'HW616' | 3.0 ± 0.1 | 19 |
| 'Bartlett' | 3.3 ± 0.1 | 13 |
| 'Harrow' 'Delight' | 3.1 ± 0.2 | 13 |
| 'Harrow Sweet' | 3.1 ± 0.1 | 15 |
| 'Harvest Queen' | 3.7 ± 0.2 | 17 |
| 'Bosc' | 4.4 ± 0.1 | 14 |

[z]Shoots harvested in Feb., 1996, from mature trees (>10 years old) grown on 'Bartlett' seedling rootstock at Harrow, Ont., Canada.

*Seeds.*—Seed colour is dark brown when mature, the shape is egg-shaped, and size is medium-large. Fruits typically have five elongated carpels, and seed numbers per fruit typically range between 5 and 8.

*Leaves.*—The leaves are elliptic. The shape of the base of the leaf blade is right-angled. The shape of the upper part of the leaf blade is right-angled with a pointed acuminate tip. There is little curvature of the midrib. Leaf serrations are small and shallow but distinct. The angle between the petiole and the shoot is between 30° and 60°, the petiole is medium to long, and stipules are present. The attitude of the leaf in relation to the shoot is horizontal to slightly downward. Actively growing shoot tips are green with little pubescence.

*Leaves and petioles.*—Leaves and petioles: No data for leaf color, texture or leaf scars were collected from trees used for botanical description data. Leaf size data are presented in Table 2.

TABLE 2

Mean (mm ∀ SE) leaf length, width and petiole length as determined on leaves collected from the mid-portion of current season's extension growth[z]

| 'Cultivar' | Leaf length | Leaf width | Petiole length |
|---|---|---|---|
| | mm | | |
| 'HW616' | 70.2 (9.4) | 36.1 (4.7) | 21.4 (3.5) |
| 'Bartlett' | 67.0 (7.3) | 39.1 (5.2) | 17.8 (5.7) |

TABLE 2-continued

Mean (mm ∀ SE) leaf length, width and petiole length as determined on leaves collected from the mid-portion of current season's extension growth[z]

| 'Cultivar' | Leaf length | Leaf width | Petiole length |
|---|---|---|---|
| 'Harrow Delight' | 74.9 (6.9) | 37.5 (4.0) | 19.8 (3.1) |
| 'Harvest Queen' | 65.6 (8.6) | 34.7 (7.1) | 23.0 (10.3) |

[z]Leaves (1 leaf/shoot, 10 shoots/tree, 4 trees/cultivar, n = 40) were harvested Jul. 27, 1995 from trees (>8 years old) grown on 'Bartlett' seedling rootstock at Harrow, Ontario, Canada.

The adaxial surface of leaves of HW616 obtained from the mid-section of current season's extension growth from trees (~10 years old) grown on 'Bartlett' seedling rootstock at the AAFC Jordan Farm, Jordan Station, Ontario, Canada, was described using The Royal Horticultural Society Colour Chart as 137A, while the abaxial surface was described as 147B. Both adaxial and abaxial leaf surfaces were described as smooth. Flowers: At Harrow, Ontario, Canada, the date of first bloom of HW616 is about May 7 (depending on season), later than 'Harrow Delight' (~May 4) and 'Harvest Queen' and 'Bartlett' (~May 6). The date of full bloom is ~May 11, similar to 'Harrow Delight' and 'Harvest Queen' (~May 11) and earlier then 'Bartlett' (May 13). Flower descriptive data obtained at ~ full bloom are presented in Table 3.

TABLE 3

Flower characteristics of HW616 in comparison to 'Harrow Delight', 'Harvest Queen' and 'Bartlett'.

| Characteristic | 'HW616' | 'Harrow Delight' | 'Harvest Queen' | 'Bartlett' |
|---|---|---|---|---|
| Pedicel: | | | | |
| length | long | long | medium-long | medium |
| Sepal: | | | | |
| length | medium-long | long | short-medium | medium |
| position | horizontal-recurved | horizontal-recurved | horizontal-recurved | horizontal |
| Petals: | | | | |
| overlapping | touching | separate-touching | separate | separate-touching |
| length (inc. claw) | medium-long | medium-long | medium | medium |
| length/breadth | long · broad | longer > broad | long · broad | long · broad |
| shape of base (ex. claw) | u-shaped | v-shaped | u-shaped | flat or cordate |
| length of claw | medium | medium-long | short-medium | short-medium |
| undulation of margin | medium | medium | medium | medium |
| Stigma: | | | | |
| position as compared with anthers | level | level | level | below |
| Anther: | | | | |
| size | medium | medium-large | medium-large | medium |

TABLE 3-continued

Flower characteristics of HW616 in comparison to 'Harrow Delight', 'Harvest Queen' and 'Bartlett'.

| Characteristic | 'HW616' | 'Harrow Delight' | 'Harvest Queen' | 'Bartlett' |
|---|---|---|---|---|
| Receptacle: | | | | |
| shape | hollowed | hollowed | hollowed | hollowed |

*Fire blight resistance.*—As with other introductions from the Harrow pear breeding program (Hunter et al., 2002; Hunter et al., 1992; Quamme and Spearman, 1983), 'HW616' has excellent resistance to fire blight, similar to or greater than that of 'Kieffer' (unpatented) which is used as the standard for selection (Hunter, 1993). Using natural fire blight infection scores (van der Zwet et al., 1970), 'HW616' had a resistance rating similar to its parents, 'Harrow Delight' and 'Harvest Queen', and much greater than 'Bartlett' (Table 4). When actively growing shoot tips were inoculated with a mixture of six virulent strains of *E. amylovora*, the length of the lesion that developed extended to ≈25% of current season's growth, similar to 'Harrow Delight', 'Harvest Queen', and 'Kieffer' (unpatented), but much less than lesion development in 'Bartlett' (Table 4).

*Bloom and pollination.*—At Harrow, the time of full bloom of 'HW616' tree is similar to that of 'Harrow Delight' and 'Harvest Queen', and is ≈2 days earlier than 'Bartlett'. First bloom, however, is 1 day later than 'Bartlett'. Flower clusters typically contain six or seven flowers, occasionally five or eight. Petals are white (RHS color designations), almost as long as broad, and touch or slightly overlap. The pink (RHS color designations) to red (RHS color designations) anthers are medium in size, and are about level with the stigma.

In controlled pollination tests, fruit set was used to determine pollen compatibility when pollen from a known source was applied to stigmatic surfaces immediately after emasculation of the flower. Because emasculated pear flowers are even less attractive to bees and other pollinating insects than non-emasculated flowers, bagging was not considered necessary. 'HW616' appears to be reciprocally pollen compatible with 'Bartlett', 'Seckel' (unpatented), 'Old Home' (unpatented), and 'Harvest Queen'. While 'HW616' will pollinate 'Harrow Delight', 'Harrow Delight' will not pollinate 'HW616'. Results of reciprocal pollinations between 'HW616' and 'Bosc' (patented) have been variable and inconclusive.

Fruit characteristics:

*Size, shape and color.*—Fruits are medium sized, with a fruit length similar to 'Harrow Delight', longer than 'Harvest Queen', and slightly, but not significantly, smaller than 'Bartlett' (Table 3). Fruit diameter of 'HW616' was similar to 'Harvest Queen' and 'Harrow Delight' and significantly smaller than 'Bartlett'. Fruit size and weight are improved by fruit thinning. Fruit shape is symmetrical, pyriform, and slightly concave to straight in profile. Using International Board for Plant Genetic Resources descriptors (Thibault et al., 1983), the predominant fruit shape has been described as 5.2 (≈25% of individual fruits) or 5.4 (≈25%), while other individual fruits have been described as 3.3 (≈10%), 3.4 (≈15%), 7.2 (≈10%), and 7.4 (≈10%). The calyx is persistent at harvest, with medium to long sepals that are convergent to upright. The calyx basin is medium depth and narrow to medium in width, with a slightly ribbed margin. Following ripening at ≈20° C., the skin has an attractive golden yellow ground color (RHS 11A or 11B) with no more than a trace of blush on the sun-exposed fruit surface, and there is little or no russetting. The flesh is cream (RHS color designations) to cream-white (RHS color designations) in color, is exceptionally juicy, and has excellent flavor with a good balance between sweetness and acidity.

*Maturity.*—At Harrow, Ont., Canada, the fruits of 'HW616' mature about August 15, between 'Harrow Delight' and 'Harvest Queen', and ≈13 days before 'Bartlett'. Unlike 'Harrow Delight', pre-harvest fruit drop is not a problem.

*Quality.*—At Harrow, fruits were harvested each year at the normal fresh market maturity for commercial harvest (5–7 kg pressure). Following ripening at ≈20° C. until 'eating ripe', a sample of 5 to 10 fruits, selected at random, was evaluated for appearance, flavor, texture, number and size of grit (stone cells) in the flesh, juiciness, and core size relative to fruit size. Evaluations were made on fruits ripened immediately after harvest. At Harrow, trained panelists rated the appearance of ripened fruits of 'HW616' equivalent to 'Bartlett', 'Harrow Delight' and 'Harvest Queen' (Table 3). The flesh texture was excellent, with little or no grit. The fresh fruit quality rating for 'HW616', as indicated by the weighted score, was similar to 'Bartlett', 'Harrow Delight' and 'Harvest Queen' (Table 3). There were no significant differences between fruits ripened immediately after harvest and fruits ripened after 4 weeks in a common cold storage at ≈2° C. (data not presented).

*Processing evaluations.*—When ripened fruits are processed as halves or as purée, 'HW616' is rated similar to 'Harrow Delight' and 'Harvest Queen', but lower than 'Bartlett' (Table 4). While the processed product from small scale trials has been rated good, the quality may not be sufficiently high for 'HW616' to have commercial acceptability for processing in the current market. The commercial processing potential of this new cultivar will be further evaluated when the large scale plantings established in 1999 come into production.

Availability

'HW616' was tested at the Canadian Centre for Plant Health, Saanichton, B.C., using woody-host and herbaceous-host biological indicators, and by serological and molecular methods, and found to be free of all known viruses, virus-like agents, viroids and phytoplasmas. Virus-tested trees have been planted in the Canadian Clonal Gene Bank at Harrow.

TABLE 4

Ratings of natural and induced fire blight infections of 'HW616' in comparison to 'Harrow Delight', 'Harvest Queen', 'Bartlett', and 'Kieffer'.

| | 'HW616' | 'Harrow Delight' | 'Harvest Queen' | 'Bartlett' | 'Kieffer' |
|---|---|---|---|---|---|
| Natural infections[z] | | | | | |
| Rating | 9.6 ± 0.1 | 9.5 ± 0.1 | 9.1 ± 0.1 | 4.2 ± 0.4 | 9.3 ± 0.1 |
| Years evaluated | 10 | 19 | 20 | 18 | 15 |
| Induced infections[y] | | | | | |
| Lesion (% shoot length) | 24.6 ± 4.4 | 16.2 ± 3.0 | 22.0 ± 3.3 | 62.8 ± 4.2 | 23.1 ± 1.6 |
| Years evaluated | 10 | 12 | 12 | 22 | 16 |

[z]Natural fire blight infections, rated on a scale of 1 (tree dead) to 10 (no blight), are means ± SE of 10 to 20 years at Harrow, Ont., Canada. The rating system was modified from van der Zwet et al. (1970) by assigning values of 10 = no visible blight and 9 = <3% infection. For 'HW616', 'Harrow Delight', and 'Harvest Queen', ratings were made on the own-rooted seedling tree. For 'Bartlett' and 'Kieffer', ratings were made on trees grown on Bartlett seedling rootstock in a nearby (within 200 m) cultivar evaluation orchard. In both the seedling orchard and the cultivar evaluation orchard, susceptible trees had severe fire blight infections each year.
[y]Induced infections were measured in late July, ≈5 weeks after inoculating 10–20 actively growing shoots with 20 $\mu$L of a cocktail of six virulent strains of *Erwinia amylovora* ($10^8$ cfu/mL). Values indicate lesion length expressed as a percentage of total shoot length. Data are means ± SE of 10 to 22 years.

TABLE 5

Harvest dates at Harrow, Ont., Canada, and fresh fruit evaluations for 'Harrow Delight', 'AC Harrow Gold', 'Harvest Queen', and 'Bartlett'

| | 'Harrow Delight' | 'HW616' | 'Harvest Queen' | 'Bartlett' |
|---|---|---|---|---|
| Years evaluated | 22 | 12 | 21 | 20 |
| Harvest dates | | | | |
| Average | 11 Aug. | 15 Aug. | 18 Aug. | 28 Aug. |
| Earliest | 27 July | 31 July | 6 Aug. | 18 Aug. |
| Latest | 18 Aug. | 22 Aug. | 24 Aug. | 9 Sept. |
| Size (mm) | | | | |
| Length | 80.4 a[z] | 80.5 a | 72.4 b | 81.4 a |
| Diameter | 58.7 b | 59.1 b | 58.0 b | 63.4 a |
| Ratings[y] | | | | |
| Appearance[x] | 7.8 a | 7.6 a | 7.5 a | 7.7 a |
| Flavor[x] | 8.2 a | 8.0 a | 8.3 a | 8.0 a |
| Texture[x] | 8.0 ab | 8.5 a | 8.5 a | 7.9 b |
| Weighted score[w] | 82.5 a | 83.6 a | 82.9 a | 81.3 a |

TABLE 5-continued

Harvest dates at Harrow, Ont., Canada, and fresh fruit evaluations for 'Harrow Delight', 'AC Harrow Gold', 'Harvest Queen', and 'Bartlett'

| | 'Harrow Delight' | 'HW616' | 'Harvest Queen' | 'Bartlett' |
|---|---|---|---|---|
| Grit[v] | 4.1 bc | 4.4 ab | 4.6 a | 3.9 c |
| Juice[u] | 4.4 a | 4.1 ab | 4.2 ab | 3.9 b |
| Core[t] | 3.0 a | 2.7 b | 2.4 b | 3.2 a |

[z]Means separation within rows by Duncan's new multiple range test, P = 0.05. Means within rows followed by the same letter are not significantly different.
[y]Ratings reported are based on evaluations of fruits ripened immediately after harvest.
[x]Appearance, flavor and texture ratings [on a scale of 1 (least desirable) to 9 (most desirable)] were determined each year by two to four trained panelists.
[w]Weighted score = (3 × appearance) + (5 × flavor) + (2 × texture).
[v]Grit rating is on a scale of 1 (undesirable, i.e. large and/or many grit cells) to 5 (desirable, i.e., very small and/or few or not grit cells).
[u]Juiciness rating is on a scale of 1 (dry) to 5 (very juicy).
[t]Core size rating is on a scale of 1 (small) to 5 (large).

TABLE 6

Ratings of pear halves[z] and pear purée[y] processed from ripened fruits of 'AC Harrow Gold' in comparison with 'Harrow Delight', 'Harvest Queen', and 'Bartlett'.

| | 'HW616' | 'Harrow Delight' | 'Harvest Queen' | 'Bartlett' |
|---|---|---|---|---|
| Halves | 3.5 b[x] | 3.4 b | 3.5 b | 3.9 a |
| Purée | 3.3 b | 3.2 b | 3.5 b | 4.0 a |

[z]Determined with masked identity taste panels involving four trained panelists. Fruits were processed in syrup containing 15% (w/v) sugar. Processing rating for pear halves is the average of ratings for flavor, texture and appearance on a scale of 1 (least desirable) to 5 (most desirable). Samples, including a masked identity 'Bartlett' sample, were compared to a known 'Bartlett' sample. Data presented are means of 5 years.
[y]Determined with masked identity taste panels involving four trained panelists. Fruits were processed with no additional sugar. Processing rating for purée is the average of ratings for viscosity, color, and flavor on a scale of 1 (least desirable) to 5 (most desirable). Samples, including a masked identity 'Bartlett' sample, were compared to a known 'Bartlett' sample. Data presented are means of 5 years.
[x]Means separation within rows by Duncan's new multiple range test, P = 0.05. Means within rows followed by the same letter are not significantly different.

In the 5th leaf, trees of HW616 grown on 'Bartlett' seedling rootstock had a trunk cross sectional area (TCSA) of 22.4∀5.9 $cm^2$ (n=4), while 'Bartlett' on 'Bartlett' seedling rootstock in the same planting had a TCSA of 16.8∀2.7 $cm^2$ (n=3). By the $8^{th}$ leaf, TCSAs were 59.2∀13.5 $cm^2$ for HW616 and 41.5∀2.7 $cm^2$ for 'Bartlett'.

What is claimed is:

1. A new and distinct variety of pear tree substantially as shown and described herein.

* * * * *